United States Patent [19]

Agui et al.

[11] 4,343,801
[45] Aug. 10, 1982

[54] 1,2,4-TRIAZINE DERIVATIVES, AND THEIR PRODUCTION AND USE

[75] Inventors: Hideo Agui, Sonehigashi; Katsumi Tamoto, Hyogo; Shunji Aono, Osaka; Takao Okuda, Sonehigashi, all of Japan

[73] Assignee: Sumitomo Chemical Company, Limited, Osaka, Japan

[21] Appl. No.: 212,442

[22] Filed: Dec. 3, 1980

[30] Foreign Application Priority Data

Dec. 3, 1979 [JP] Japan .................................. 54/157249
Sep. 27, 1980 [JP] Japan .................................. 55/133348

[51] Int. Cl.³ .................... C07D 401/04; A01N 43/64; C07D 401/14; A01N 43/10
[52] U.S. Cl. ..................................... 424/249; 544/182
[58] Field of Search .......................... 544/182; 424/249

[56] References Cited

U.S. PATENT DOCUMENTS 4,033,752  7/1977  Hashimoto et al. ................. 544/182
4,081,267  3/1978  Hashimoto et al. ................. 544/182

FOREIGN PATENT DOCUMENTS 2602186  7/1976  Fed. Rep. of Germany ...... 544/182

Primary Examiner—John M. Ford
Attorney, Agent, or Firm—Birch, Stewart, Kolasch and Birch

[57] ABSTRACT

A compound of the formula:

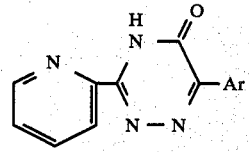

wherein Ar is a phenyl group substituted with halogen, $C_1$–$C_8$ alkyl, $C_1$–$C_8$ alkoxy, $C_1$–$C_8$ alkylthio, $C_1$–$C_8$ alkylsulfonyl, nitro, trihalomethyl, cyano, $C_1$–$C_8$ alkylamino, di($C_1$–$C_8$)-alkylamino, amino, hydroxyl, phenyl and/or phenoxy, a naphthyl group or a thienyl group optionally substituted with halogen, which is useful as an antifungal agent.

18 Claims, No Drawings

1,2,4-TRIAZINE DERIVATIVES, AND THEIR PRODUCTION AND USE

The present invention relates to 1,2,4-triazine derivatives, and their production and use. More particularly, it relates to 1,2,4-triazine derivatives of the formula:

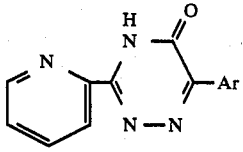

wherein Ar is a phenyl group substituted with halogen, $C_1$–$C_8$ alkyl, $C_1$–$C_8$ alkoxy, $C_1$–$C_8$ alkylthio, $C_1$–$C_8$ alkylsulfonyl, nitro, trihalomethyl, cyano, $C_1$–$C_8$ alkylamino, di($C_1$–$C_8$)-alkylamino, amino, hydroxyl, phenyl and/or phenoxy, a naphthyl group or a thienyl group optionally substituted with halogen, their preparation process and their antifungal use.

In the above significances, the alkyl moiety may be straight or branched, and can cover methyl, ethyl, n-propyl, iso-propyl, n-butyl, iso-butyl, tert-butyl, n-pentyl, n-hexyl, n-heptyl, n-octyl, etc. Among the alkyl moieties, those having 1 to 4 carbon atoms are preferred. The number of the substituent(s) which should be present on the phenyl group or may be present on the thienyl group is usually not more than 3.

The said 1,2,4-triazine derivatives (I) can be prepared, for instance, by reacting a keto-carboxylic acid or its ester of the formula:

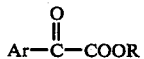

wherein R is a hydrogen atom or a $C_1$–$C_4$ alkyl group and Ar is as defined above, with 2-pyridylhydrazidine of the formula:

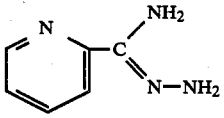

The keto-carboxylic acid or its ester (II) is known or can be easily prepared by a per se known procedure as described in "Organic Syntheses" Coll. Vol. 1, 241 (1941). The 2-pyridylhydrazidine (III) is known and described in J. Org. Chem., 30, 931 (1965).

The reaction is readily carried out by treating the keto-carboxylic acid or its ester (II) with 2-pyridylhydrazidine (III), usually in an equimolar proportion. It is particularly preferred to effect the treatment in an inert solvent such as an alkanol (e.g. methanol, ethanol), an ether (e.g. tetrahydrofuran, dioxane), a halogenated hydrocarbon (e.g. carbon tetrachloride, methylene chloride), dimethylformamide or water at a temperature between 0° C. and 300° C., especially between 60° C. and 200° C.

The said reaction between the keto-carboxylic acid or its ester (II) and 2-pyridylhydrazidine (III) may be considered to proceed through the following intermediary compound:

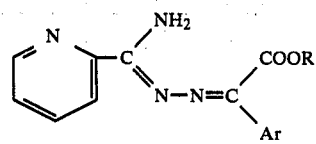

wherein Ar and R are each as defined above. When the keto-carboxylic acid (II: R=H) is used as the starting material, its reaction with 2-pyridylhydrazidine (III) at a temperature not higher than room temperature can afford the corresponding compound (IV: R=H), which may be heated, with or without isolation from the reaction mixture, above room temperature to give the objective 1,2,4-triazine derivative (I) with ease. When the keto-carboxylic acid (II: R=H) is reacted with 2-pyridylhydrazidine (III) under heating, the corresponding intermediary compound (IV: R=H) is hardly isolated, and the objective 1,2,4-triazine derivative (I) is directly produced. In case of the starting material being the keto-carboxylic ester (II: R=$C_1$–$C_4$ alkyl), the corresponding intermediary compound (IV: R=$C_1$–$C_4$ alkyl) is hardly produced even when the reaction is effected at low temperature, and there is obtained directly the objective 1,2,4-triazine derivative (I).

The 1,2,4-triazine derivatives (I) of the invention are novel and exhibit a strong antifungal activity against pathogenic fungi as shown in Table 1:

TABLE 1

Antifungal activity in vitro 1,2,4-Triazine derivative (I)

| Ar | Minimum inhibitory concentration (μg/ml) | |
|---|---|---|
| | *Trichophyton rubrum* | *Candida albicans* |
| 2-F-C₆H₄ | 10 | 20–100 |
| 3-F-C₆H₄ | 1.25 | 20 |
| 4-F-C₆H₄ | 0.6 | 10 |
| 2-Cl-C₆H₄ | 20 | 20–100 |
| 3-Cl-C₆H₄ | 0.6 | 20 |
| 4-Cl-C₆H₄ | 0.6 | 10 |
| 4-Br-C₆H₄ | 0.6 | 20 |

TABLE 1-continued
Antifungal activity in vitro

| 1,2,4-Triazine derivative (I) Ar | Minimum inhibitory concentration (μg/ml) Trichophyton rubrum | Candida albicans |
|---|---|---|
| —C₆H₄—I (4-) | 0.6 | 20–100 |
| 2,4-F₂-C₆H₃— | 2.5 | 100 |
| 2-F, 3-Cl-C₆H₃— | 20–100 | 100 |
| 2,4-Cl₂-C₆H₃— | 2.5 | 20–100 |
| 2,3-Cl₂-C₆H₃— | 0.3 | 20–100 |
| —C₆H₄—CH₃ (4-) | 1.25 | 20–100 |
| —C₆H₄—OCH₃ (4-) | 2.5 | 20–100 |
| 2,3-(OCH₃)₂-C₆H₃— | 20 | 20–100 |
| —C₆H₄—SCH₃ (4-) | 2.5 | 20–100 |
| —C₆H₄—SO₂CH₃ (4-) | 20–100 | 100 |
| —C₆H₄—NO₂ (3-) | 20–100 | 100 |
| —C₆H₄—NO₂ (4-) | 20 | 100 |
| —C₆H₄—CF₃ (3-) | 2.5 | 5 |
| —C₆H₄—CF₃ (4-) | 1.25 | 20–100 |
| —C₆H₄—CN (4-) | 1.25 | 20–100 |
| —C₆H₄—N(CH₃)₂ (4-) | 2.5 | 100 |
| —C₆H₄—OH (4-) | 20–100 | 20–100 |
| —C₆H₄—NH₂ (4-) | 20 | 20–100 |
| —C₆H₄—C₆H₅ (4-) | 5 | 100 |
| —C₆H₄—O—C₆H₅ (3-) | 20 | 20 |
| —C₆H₄—O—C₆H₅ (4-) | 20 | 20 |
| 2-naphthyl | 20 | 100 |
| 2-thienyl | 0.6 | 20 |
| 5-chloro-2-thienyl | 20 | 20 |
| 3-bromo-2-thienyl | 2.5 | 100 |

Thus, the 1,2,4-triazine derivatives (I) of the invention are useful as antifungal agents. They can be administered parenterally, orally or locally to warm-blooded animals in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 10 mg to 5 g.

Practical and presently preferred embodiments of the invention are illustratively shown in the following Examples, which are not intended to limit the scope of the invention thereto.

EXAMPLE 1

A mixture of 0.68 g (0.005 mol) of 2-pyridylhydrazidine, 0.95 g (0.005 mol) of 4-chlorophenylglyoxylic acid and 10 ml of ethanol was stirred at room temperature for 15 hours, and precipitated crystals were collected by filtration. The crystals were dissolved in 10 ml of dimethylformamide, and the resulting solution was stirred at 100° to 120° C. for 4 hours. The solvent was evaporated off, and the residue was recrystallized from ethanol to give 0.95 g of 6-(4-chlorophenyl)-3-(2-pyridyl)-1,2,4-triazin-5(4H)-one as yellow needles melting at 216°–217° C.

Elementary analysis for $C_{14}H_9N_4OCl$ (%): Calcd.: C, 59.06; H, 3.19; N, 19.68; Found: C, 59.20; H, 3.00; N, 19.96.

EXAMPLE 2

A mixture of 0.68 g (0.005 mol) of 2-pyridylhydrazidine, 0.95 g (0.005 mol) of 4-chlorophenylglyoxylic acid and 50 ml of ethanol was heated under reflux for 5 hours. The reaction mixture was cooled, and precipitated crystals of 6-(4-chlorophenyl)-3-(2-pyridyl)-1,2,4-triazin-5(4H)-one were collected by filtration. The infrared spectrum and melting point of the crystals were consistent with those of the product in Example 1.

EXAMPLE 3

A mixture of 0.68 g (0.005 mol) of 2-pyridylhydrazidine, 1.06 g (0.005 mol) of ethyl 4-chlorophenylglyoxylate and 50 ml of ethanol was heated under reflux for 5 hours. The reaction mixture was filtered while hot to remove 5-(4-chlorophenyl)-3-(2-pyridyl)-1,2,4-triazin-6(1H)-one, which is an isomer of the desired product. The filtrate was cooled, and precipitated crystals of 6-(4-chlorophenyl)-3-(2-pyridyl)-1,2,4-triazin-5(4H)-one were collected by filtration. The infrared spectrum and melting point of the crystals were consistent with those of the product in Example 1.

EXAMPLE 4

A mixture of 0.68 g (0.005 mol) of 2-pyridylhydrazidine, 1.06 g (0.005 mol) of ethyl 4-chlorophenylglyoxylate and 50 ml of ethanol was stirred under ice-cooling for 5 hours and at room temperature for 10 hours. Crystals of 6-(4-chlorophenyl)-3-(2-pyridyl)-1,2,4-triazin-5(4H)-one were precipitated from the reaction mixture and collected by filtration. The infrared spectrum and melting point of the crystals were consistent with those of the product in Example 1.

In the same manner as in Example 1, the following compounds were obtained:

6-(2-Chlorophenyl)-3-(2-pyridyl)-1,2,4-triazin-5(4H)-one, M.P., 168°–169° C.;
6-(3-Chlorophenyl)-3-(2-pyridyl)-1,2,4-triazin-5(4H)-one, M.P., 186°–187° C.;
6-(2-Fluorophenyl)-3-(2-pyridyl)-1,2,4-triazin-5(4H)-one, M.P., 178°–181° C.;
6-(3-Fluorophenyl)-3-(2-pyridyl)-1,2,4-triazin-5(4H)-one, M.P., 198°–199° C.;
6-(4-Fluorophenyl)-3-(2-pyridyl)-1,2,4-triazin-5(4H)-one, M.P., 191°–192° C.;
6-(4-Bromophenyl)-3-(2-pyridyl)-1,2,4-triazin-5(4H)-one, M.P. 222°–224° C.;
6-(4-Iodophenyl)-3-(2-pyridyl)-1,2,4-triazin-5(4H)-one, M.P. 224°–225° C.;
6-(2,4-Dichlorophenyl)-3-(2-pyridyl)-1,2,4-triazin-5(4H)-one, M.P., 214°–215° C.;
6-(3,4-Dichlorophenyl)-3-(2-pyridyl)-1,2,4-triazin-5(4H)-one, M.P. 249°–250° C.;
6-(2,4-Difluorophenyl)-3-(2-pyridyl)-1,2,4-triazin-5(4H)-one, M.P. 217°–218° C.;
6-(2-Chloro-6-fluorophenyl)-3-(2-pyridyl)-1,2,4-triazin-5(4H)-one, M.P. 199°–202° C.;
6-(4-Methylphenyl)-3-(2-pyridyl)-1,2,4-triazin-5(4H)-one, M.P. 165°–166° C.;
6-(4-Methoxyphenyl)-3-(2-pyridyl)-1,2,4-triazin-5(4H)-one, M.P., 184°–185° C.;
6-(4-Methylthiophenyl)-3-(2-pyridyl)-1,2,4-triazin-5(4H)-one, M.P., 188°–190° C.;
6-(4-Mesylphenyl)-3-(2-pyridyl)-1,2,4-triazin-5(4H)-one, M.P., 252°–253° C.;
6-(3-Nitrophenyl)-3-(2-pyridyl)-1,2,4-triazin-5(4H)-one, M.P., 289°–290° C.;
6-(4-Nitrophenyl)-3-(2-pyridyl)-1,2,4-triazin-5(4H)-one, M.P., 243°–245° C.;
6-(3-Trifluoromethylphenyl)-3-(2-pyridyl)-1,2,4-triazin-5(4H)-one, M.P., 178°–181° C.;
6-(4-Trifluoromethylphenyl)-3-(2-pyridyl)-1,2,4-triazin-5(4H)-one, M.P., 231°–232° C.;
6-(4-Cyanophenyl)-3-(2-pyridyl)-1,2,4-triazin-5(4H)-one, M.P., 252°–254° C.;
6-(4-Dimethylaminophenyl)-3-(2-pyridyl)-1,2,4-triazin-5(4H)-one, M.P., 250° C.;
6-(3,4-Dimethoxyphenyl)-3-(2-pyridyl)-1,2,4-triazin-5(4H)-one, M.P., 193°–195° C.;
6-(4-Hydroxyphenyl)-3-(2-pyridyl)-1,2,4-triazin-5(4H)-one, M.P. 210° C.;
6-(4-Aminophenyl)-3-(2-pyridyl)-1,2,4-triazin-5(4H)-one, M.P. 215°–217° C.;
6-(4-Phenylphenyl)-3-(2-pyridyl)-1,2,4-triazin-5(4H)-one, M.P. 200°–203° C.;
6-(4-Phenoxyphenyl)-3-(2-pyridyl)-1,2,4-triazin-5(4H)-one, M.P., 178°–181° C.;
6-(3-Phenoxyphenyl)-3-(2-pyridyl)-1,2,4-triazin-5(4H)-one, M.P., 146°–148° C.;
6-(2-Naphthyl)-3-(2-pyridyl)-1,2,4-triazin-5(4H)-one, M.P., 185°–186° C.;
6-(2-Thienyl)-3-(2-pyridyl)-1,2,4-triazin-5(4H)-one, M.P., 220°–222° C.;
6-(5-Chloro-2-thienyl)-3-(2-pyridyl)-1,2,4-triazin-5-(4H)-one, M.P., 217°–219° C.;
6-(3-Bromo-2-thienyl)-3-(2-pyridyl)-1,2,4-triazin-5(4H)-one, M.P., 198°–201° C.

What is claimed is:

1. A compound of the formula:

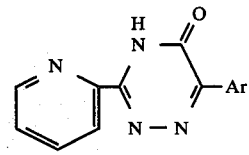

wherein Ar is a phenyl group substituted with a member selected from the group consisting of halogen, $C_1$–$C_8$ alkyl, $C_1$–$C_8$ alkoxy, $C_1$–$C_8$ alkylthio, trihalomethyl, cyano, and phenoxy, or a thienyl group substituted with halogen.

2. The compound according to claim 1, wherein Ar is a phenyl group substituted with halogen.

3. The compound according to claim 2, wherein Ar is 3-fluorophenyl.

4. The compound according to claim 2, wherein Ar is 4-fluorophenyl.

5. The compound according to claim 2, wherein Ar is 3-chlorophenyl.

6. The compound according to claim 2, wherein Ar is 4-chlorophenyl.

7. The compound according to claim 2, wherein Ar is 3,4-dichlorophenyl.

8. The compound according to claim 2, wherein Ar is 4-bromophenyl.

9. The compound according to claim 2, wherein Ar is 4-iodophenyl.

10. The compound according to claim 1, wherein Ar is a phenyl group substituted with $C_1$–$C_8$ alkyl.

11. The compound according to claim 10, wherein Ar is 4-methylphenyl.

12. The compound according to claim 1, wherein Ar is a phenyl group substituted with trihalomethyl.

13. The compound according to claim 12, wherein Ar is 3-trifluoromethylphenyl.

14. An antifungal composition which comprises as an active ingredient an antifungally effective amount of the compound as claimed in claim 1, and an inert carrier or diluent.

15. A compound of the formula:

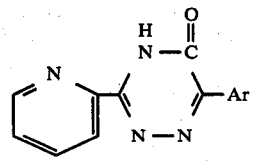

wherein Ar is a thienyl group or a thienyl group substituted with halogen.

16. A method of destroying fungi which comprises applying a fungicidal amount of the compound of claim 1 to fungi.

17. A fungicidal composition which comprises as an active ingredient a fungicidal amount of the compound of claim 15, and an inert carrier or diluent.

18. A method of destroying fungi which comprises applying a fungicidal amount of the compound of claim 15 to fungi.

* * * * *

UNITED STATES PATENT AND TRADEMARK OFFICE
CERTIFICATE OF CORRECTION

PATENT NO. : 4,343,801

DATED : August 10, 1982

INVENTOR(S) : Agui et al

It is certified that error appears in the above—identified patent and that said Letters Patent is hereby corrected as shown below:

On the title page:

In the category "[30] Foreign Application Priority Data", change "Sep. 27, 1980 [JP] Japan .... 55/133348" to --Sep. 24, 1980 [JP] Japan .... 55/133348--.

Signed and Sealed this

Nineteenth Day of October 1982

[SEAL]

Attest:

Attesting Officer

GERALD J. MOSSINGHOFF

Commissioner of Patents and Trademarks